United States Patent [19]

Geiger

[11] 4,034,601

[45] July 12, 1977

[54] METHOD AND APPARATUS FOR DETERMINING COAGULATION TIMES

[75] Inventor: Mario Theodore Geiger, Wettingen, Switzerland

[73] Assignee: American Hospital Supply Corporation, Evanston, Ill.

[21] Appl. No.: 675,936

[22] Filed: Apr. 12, 1976

Related U.S. Application Data

[63] Continuation of Ser. No. 500,911, Aug. 27, 1974, abandoned.

[51] Int. Cl.² .................. G01N 11/10; G01N 33/16

[52] U.S. Cl. ................................ 73/64.1; 23/230 B

[58] Field of Search ................ 73/64.1; 356/36, 39; 23/230 B

[56] References Cited

U.S. PATENT DOCUMENTS

| | | | |
|---|---|---|---|
| 3,020,748 | 2/1962 | Marshall et al. | 73/64.1 |
| 3,267,362 | 8/1966 | Page | 23/253 R |
| 3,267,363 | 8/1966 | Young | 23/253 R |
| 3,267,364 | 8/1966 | Page et al. | 23/253 R |
| 3,814,585 | 6/1974 | Bailly | 73/64.1 X |

*Primary Examiner*—Richard C. Queisser
*Assistant Examiner*—Joseph W. Roskos
*Attorney, Agent, or Firm*—Tilton, Fallon, Lungmus, Chestnut & Hill

[57] ABSTRACT

A method and apparatus for determining coagulation times in such clinical laboratory procedures as prothrombin times tests, activated partial thromboplastin time tests, fibrinogen determinations, factor assays for specific blood coagulation factors, and the like. A fibrous filament is drawn at a predetermined rate through a small body of liquid to be tested and the interval, from the time a suitable coagulating agent is mixed with the liquid to the time the body of liquid clings to the filament and moves with it, is precisely measured as a direct indication of actual coagulation time. The liquid body is supported upon a non-wettable inclined surface bordered by walls defining a well for receiving the liquid and a pathway for its movement. Particularly effective results are achieved by utilizing a pair of spaced filaments moving at precisely the same rate, the filaments being bridged by a web or mass of clotted liquid when coagulation occurs. A photodetector senses movement of the clot and a timer automatically measures the time between coagulant addition and clot formation. After clot detection occurs, an arm lifts the paired filaments from the well while at the same time directing the advancing filaments through slots to strip coagulum therefrom, then lifts the filaments out of the slots to permit fresh filament sections to move into place, and finally lowers the fresh sections onto a clean inclined surface for another coagulation test. Means are also disclosed for gently agitating the coagulating agent or agents prior to admixture with the test liquid, for insuring proper suspension of the reactants, and for reducing risks of infection and cross contamination during use of the apparatus.

14 Claims, 17 Drawing Figures

STOPPED

METHOD AND APPARATUS FOR DETERMINING COAGULATION TIMES

RELATED APPLICATION

This application is a continuation of copending application Ser. No. 500,911, filed Aug. 27, 1974, and now abandoned.

BACKGROUND

Two basic objectives for any device intended for automatic measurement of coagulation times are, first, that an established endpoint in the coagulation process be precisely and immediately detected so that significant reproducible results will be obtained and, second, that there be no cross contamination or carry-over from one sample to the next. While some devices known in the past have satisfied the first of these objectives, and others the second, such devices have generally failed to achieve both. Thus, electrical coagulation detectors which measure changes in conductivity (resistance) as an indicator of clot development, and optical detectors which respond to changes in reflected or transmitted light, may present relatively few carry-over or contamination problems but, unfortunately, they generally lack precision, reliability, and reproducibility in endpoint detection. On the other hand, mechanical or electro-mechanical detectors, which usually include immersible elements and which respond more directly to changes in viscosity, are more precise in endpoint detection but clearly present substantial carry-over problems.

An early method for measuring the coagulation time of freshly-drawn whole blood was that of H. Vierodt [1878, Arch. f (physiologische) Heilkunde Vol. 19]who disclosed drawing a natural filament (a meticulously cleaned white horse hair) through a glass tube containing raw blood and determining the coagulation endpoint by observing when the filament became reddish (because of red cells clinging thereto) or the coagulum (fibrin) attached itself to the moving filament. In 1910 K. Kottman and A. Lindsky [Zeitschzift fur Klinische Medizin 69:431–434 (1910)]modified Vierordt's method by incorporating thermoregulation, and in 1921 R. Schmidt [Medizinisch Klinik 17. Jahrgang Nr. 16, 459–60 (1921)] altered the thermoregulation aspect by using a U-tube instead of the straight tubes used by Vierordt and by Kottmann and Lindsky.

While Vierordt's approach may still be suitable for so-called global assays in which the coagulation time of freshly-drawn whole blood is determined, and in which the coagulation time is measured in minutes, it is not suitable for the more specific coagulation tests, such as prothrombin time test and activated partial thromboplastin time tests, where results are measured in seconds, and even in fractions of seconds, following the addition of a coagulating agent to a plasma sample. Despite considerable activity in this field, prior efforts have failed to produce a precise and reliable automatic method for measuring coagulation times, particularly for the specific assays so widely used in clinical laboratories.

The following references, and the citations therein, further indicate the state of development of the prior art: U.S. Pats. Nos. 3,766,774, 3,658,480, 3,605,010, 3,267,364, 3,268,804, 3,704,099, 3,267,363, 3,020,748, 3,077,106, 3,038,327, 3,518,057, 3,560,162, 3,525,254, 3,458,287, and 3,492,096.

SUMMARY OF INVENTION

This invention is concerned with a method and apparatus capable of achieving both of the objectives described above and, therefore, of overcoming the aforementioned limitations and deficiencies of prior methods and equipment.

In its basic form, the apparatus includes a generally smooth non-wettable surface for supporting a drop or small body of liquid (i.e., blood or plasma); a pathway along that surface leading from the point or station at which the liquid body rests; a fibrous filament having a continuous series of sections, the filament being supported so that one of its sections may be drawn through a single liquid body and along the pathway at a predetermined uniform velocity; means, generally in the form of supply and take-up spools, for supporting the filament; and a drive mechanism for advancing a section of the filament at predetermined constant (or controlled variable) velocity through the liquid body from the moment that a reagent capable of initiating coagulation is added to the liquid body and until the coagulation process has reached the point at which the body clings to the filament and commences moving along the pathway. Such movement may be detected visually or, in the case of a more fully automated unit, by a suitable photodetector. Commencement of clot movement with the filament constitutes a definite and readily ascertainable endpoint and the uninterrupted movement of the filament during the coagulation process contributes in producing a test which is highly sensitive and which yields reproducible and accurate results.

After one test is completed, the non-wettable surface is indexed laterally, the filament is advanced to present a clean section, another body of test fluid is applied to the surface, and the coagulation-initiating and testing sequence is repeated. The filament is sufficiently long to be used for a large number of such tests, although each section if used only for a single test and, after all sections have been so used, the entire filament is discarded.

The apparatus and method disclosed in this application, as representing the best mode for practicing the invention (as specifically claimed herein) of which applicant is presently aware, are also disclosed in co-owned application Ser. No. 590,911, filed on this same date in the names of B. E. Albright and S. M. Meginniss III, and now U.S. Pat. No. 3,963,349.

Other advantages and objects of the invention will become apparent as the specification proceeds.

DRAWINGS

DETAILED DESCRIPTION

Figure 1:
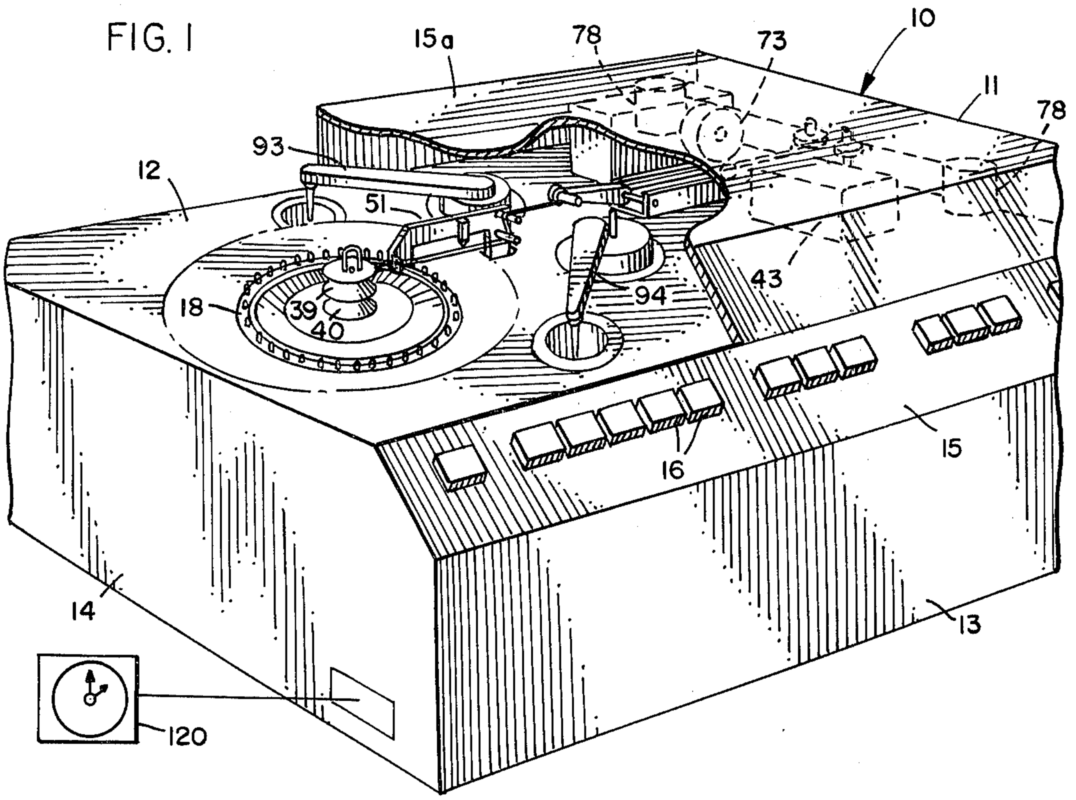
FIG. 1 is a perspective view of an apparatus embodying the invention, the apparatus casing being partly broken away to reveal internal components.

Referring to the drawings, the numeral 10 generally designates an apparatus embodying the present invention, the apparatus including a casing 11 having a top panel 12, vertical front and side panels 13 and 14, a sloping control panel 15 and a removable cover **15*a* (a portion of which is shown in phantom and may, if desired bé formed of transparent material). An array of control buttons 16** is located along the control panel, the number and purpose of such buttons being variable depending on the particular type of coagulation tests which the apparatus is adapted to perform. For clinical laboratory use, the apparatus may be programmed to conduct prothrombin time (PT) tests, activated partial thromboplastin time (APTT) tests, fibrinogen determinations, factor assays for blood coagulation factors II, V, VII, VIII, IX, X, XI and XII, and identification and plasma assays. Since the circuitry and details of the programming constitute no part of this invention, further discussion of the controls is believed unnecessary herein.

Figure 10:
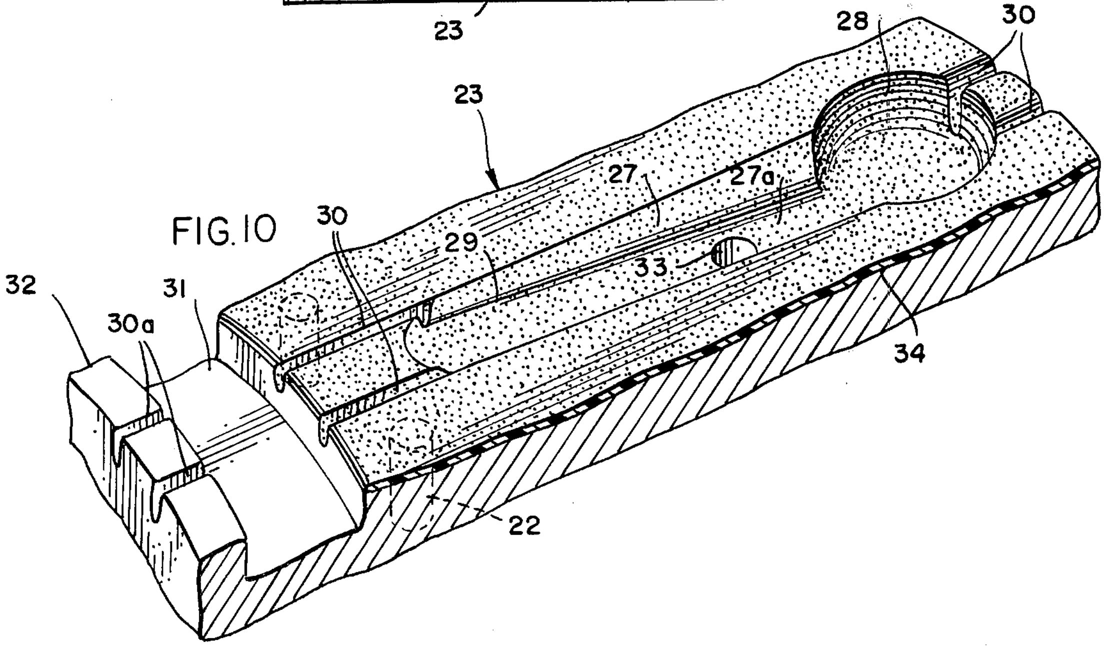
FIG. 10 is an enlarged fragmentary perspective view illustrating a portion of a sample tray.
Figure 13:
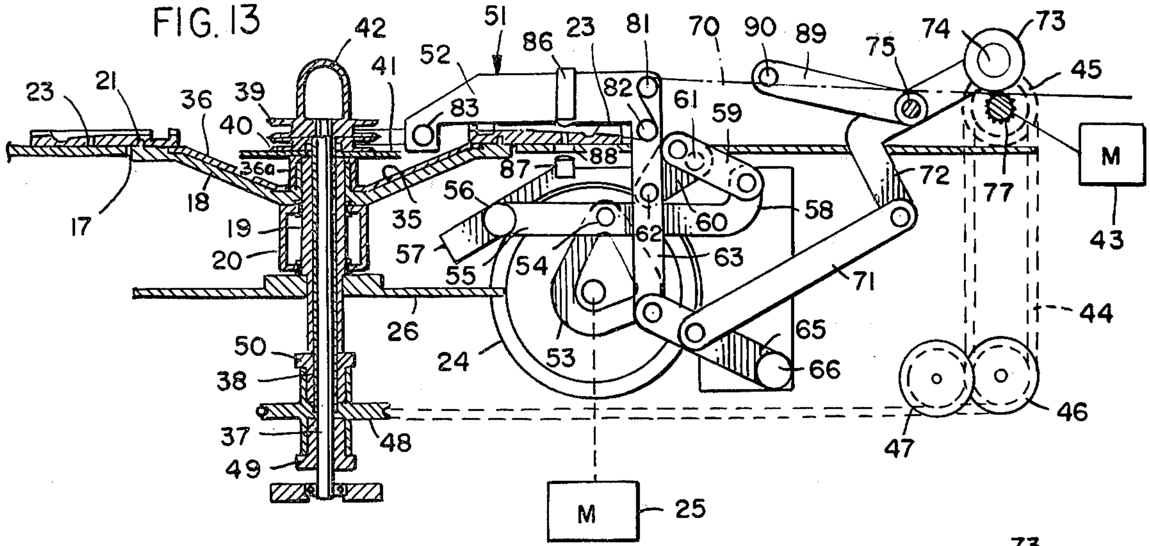
FIGS. 13–15 are somewhat schematic sectional views illustrating the relationship of parts of the apparatus during coagulation time measurement (FIG. 13), during removal of a clot from the filament (FIG. 14), and during indexing of the turntable and further advancement of the filament (FIG. 15).

The top panel is provided with a central opening 17 in which is located a turntable 18 carried by sleeve 19 which is in turn journaled in rigid frame members 20 (FIG. 13). The upper peripheral surface of the turntable is provided with a series of upstanding circumferentially-spaced pins 21 adapted to be received in openings 22 (FIG. 10) in the undersides of arcuate trays 23 for releasably supporting the trays upon the turntable for rotation therewith. It will be observed from FIG. 13 that the upper surface of the turntable is flush with the top panel 12 and that arcuate trays 23 project outwardly beyond the turntable and are slidably supported directly by the top surface of panel 12. Such a construction is advantageous because it assures precise orientation of the trays with respect to the top surface and because the direct contact between the trays and top panel permits the direct transmission of heat for maintaining the trays at proper temperature for conducting the tests, such heat being supplied by suitable heating means within the casing directly below top panel 12 (not shown).

The turntable is indexed in one direction by a stepping cam 24, driven intermittently by motor 25, which has its peripheral edge received in the notches between the teeth of wheel 26 secured to sleeve 19. Any other suitable intermittent drive mechanism, all as well known in the art, may be used for indexing turntable 18 and the trays 23 connected thereto.

In the particular embodiment illustrated in the drawings each tray 23 is provided with a plurality of adjacent recesses 27 having bottom surfaces **27*a* which slope upwardly and inwardly. Each recess is enlarged at its outer end to define a well portion 28, the well communicating directly with the narrower sloping pathway 29 and bottom surface 27*a* being common to both portions. As shown most clearly in FIG. 10, a pair of parallel grooves 30 are formed in the top of the tray along each recess 27, the grooves communicating with well 28 and pathway 29 for the purpose of guiding a pair of filaments in precisely spaced relationship through each recess 27. Also, since the grooves or notches 30 have their lower end terminating above the bottom surface 27*a*** of the recess, such grooves contribute in precisely maintaining the filaments at a slight but definite distance above that surface.

Each tray is provided along its inner edge — that is, the edge closest to the axis of the turntable — with a trough or channel 31 bordered by an upstanding inner barrier wall 32 having notches or grooves **30*a* aligned with the grooves 30 communicating with recess 27. Within each recess is a vertical passage 33 dimensioned and arranged to permit the passage of light therethrough without allowing the escape of coagulated fluid. The surface of each recess, and preferably the top portion of the tray adjacent each recess, is coated at 34 (FIG. 10**) with a suitable hydrophobic material. While waxes, silicone, and other non-wetting materials might be suitable, it has been discovered that silane-treated fumed silica, available as Silanox from Cabot Corporation of Boston, Massachusetts, is uniquely effective because of its superhydrophobicity, the uniformity of that hydrophobicity, the hardness of the coating, and the temperature stability of the coating layer. Unlike other hydrophobic surfaces, the silica-treated surface comprises a multiplicity of fumed silica microparticles which provide a macroscopically-smooth (and hence referred to herein as generally smooth) but microscopically-uneven support for the body of fluid. Such body is supported and rides only upon the projecting tops of the fumed silica particles to greatly reduce contact area and resistance to movement of the body along the non-wettable surface.

Referring to FIG. 13, it will be observed that turntable 18 is dish-shaped, having a downwardly and inwardly sloping wall portion which defines an upwardly-facing annular recess 35. A removable and disposable drip pan 36 lines the recess and, as shown in the drawings, is provided with an upstanding collar **36*a*** which extends about the hub portion of the turntable. While the liner may be formed of any suitable material, plastics such as polystyrene or polypropylene are believed particularly effective.

Figure 16:
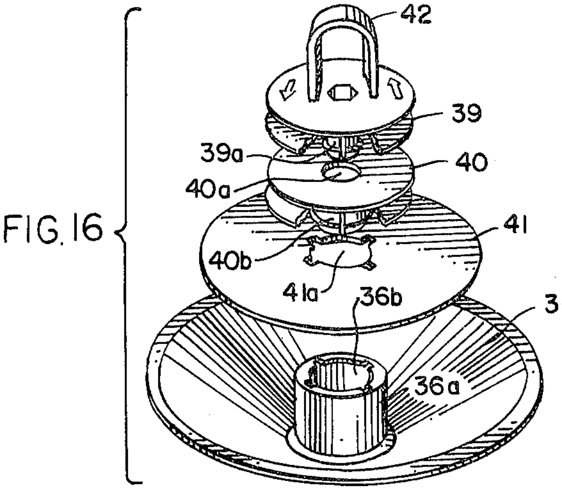
FIG. 16 is an exploded perspective view illustrating the disposable take-up reel and drip pan assembly.

A pair of coaxial shafts 37 and 38 are journaled in sleeve 19 of the turntable. The upper ends of the shafts project above the plane of top panel 12 and are non-circular (i.e., hexagonal) in configuration. A pair of reels 39 and 40 are removably fitted upon the upper ends of shafts 37 and 38, respectively, and a disk-shaped shield 41 is interposed between the reels and the upstanding collar **36*a* of the liner or drip pan 36. Like the drip pan, reels 39 and 40 and shield 41 may all be formed of plastic materials and are therefore disposable by incineration. The entire drip pan and take-up reel assembly is illustrated in exploded perspective view in FIG. 16. Interconnection of the parts to provide a unitary assembly is achieved by providing upper reel 39 with a notched depending flanged sleeve 39a which is snap fitted into opening 40a of lower reel 40. Similarly, the lower reel is provided with a depending flanged and notched sleeve 40b which extends through central opening 41a in the shield and into opening 36b at the upper end of collar 36a of the drip pan 36. The flanged sleeves prevent axial separation of the parts without preventing independent relative rotation of those parts. Preferably, the upper reel 39 is provided with a handle 42** to facilitate removal of the entire drip pan and reel assembly when replacement is required.

As already described, upper reel 39 is carried by shaft 37 and lower reel 40 is carried by shaft 38. The two shafts are driven by a motor 43 with power transmitted by a belt 44 entrained about pulleys 45–48. Pulley 48 is associated with slip clutch assemblies 49 and 50 of conventional construction. Because of the slip clutch assemblies, the rotational speed of the reels 39 and 40, and the shafts on which they are mounted, may be reduced by reason of load resistance without slowing belt 44 or motor 43.

Figure 14:
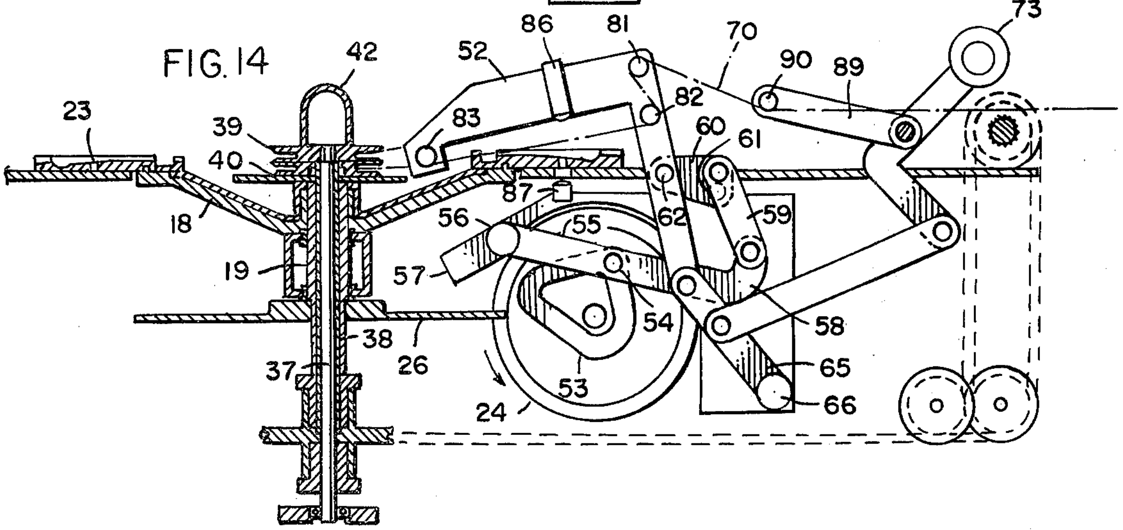
Figure 15:
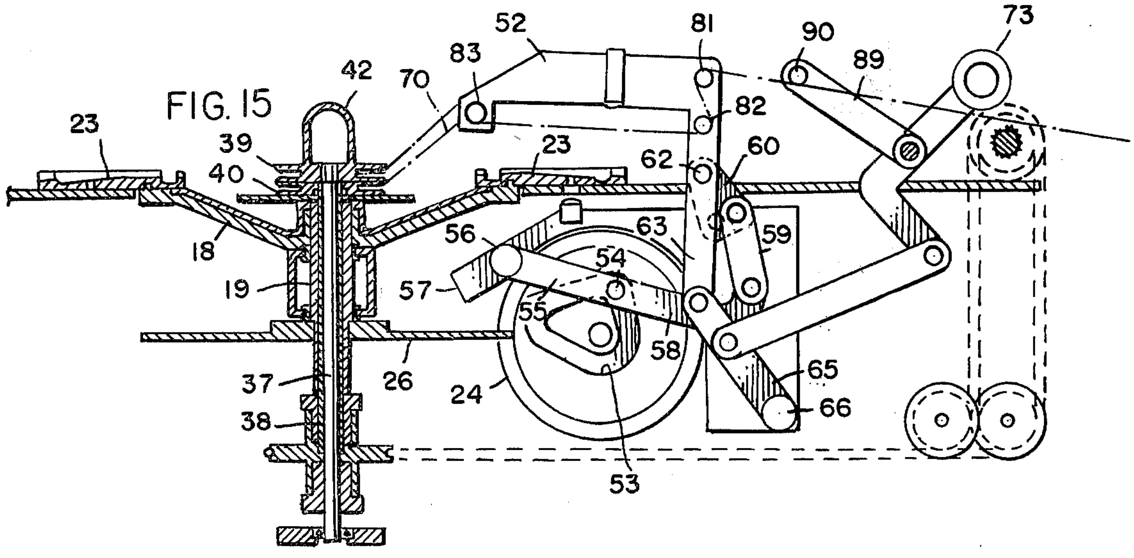

The indexing or stepping cam 24 (FIGS. 13–15) not only advances turntable gear 26 an angular distance equal to the width of a gear tooth each time the cam executes one revolution, but also cooperates with a guide arm assembly 51 to shift arm 52 into each of the three positions illustrated in FIGS. 13–15. Specifically, the face of cam 24 is provided with a groove 53, and a rider 54, carried by link 55, travels in the groove as the cam rotates. Link 55 is pivotally connected at one end 56 to frame member 57; thus, as the cam rotates, the opposite end 58 of link 55 swings upwardly and downwardly into the positions illustrated. End 58 of link 55 is connected to link 59 which is in turn connected to link 60. Link 60 is pivotally mounted on the frame at pivot point 61 and is also connected at point 62 to the depending portion 63 of guide arm 52. The depending extension 63 of the guide arm is pivotally connected to link 65, the latter being connected to the frame at pivot point 66. The result is that as the indexing cam rotates, the main portion of guide arm 52 disposed above top panel 12 and turntable 18 shifts between a lowered first position (FIG. 13) in which it is generally horizontal and is in close proximity to a tray supported by the turntable, an inclined second position (FIG. 14) in which its free end remains lowered but its rear portion lifts upwardly away from the tray, and a raised third position (FIG. 15) in which the arm is again horizontal but is spaced well above the turntable and tray.

The guide arm assembly 51, including its link arrangement, is coordinated with means for precisely controlling the rate of movement of fibrous filaments 70 and for intermittently permitting rapid advancement of those filaments. Referring to FIG. 13, it will be noted that link 71 extends between link 65 and one end of an L-shaped roller support member 72. A resilient roller 73 is carried by a horizontal shaft 74 at the free end of the support member and, as shown most clearly in FIGS. 3 and 13, that member is mounted for tipping movement (as link 65 is raised and lowered) by horizontal bar 75 secured to a pair of upstanding flanges 76.

Figure 3:
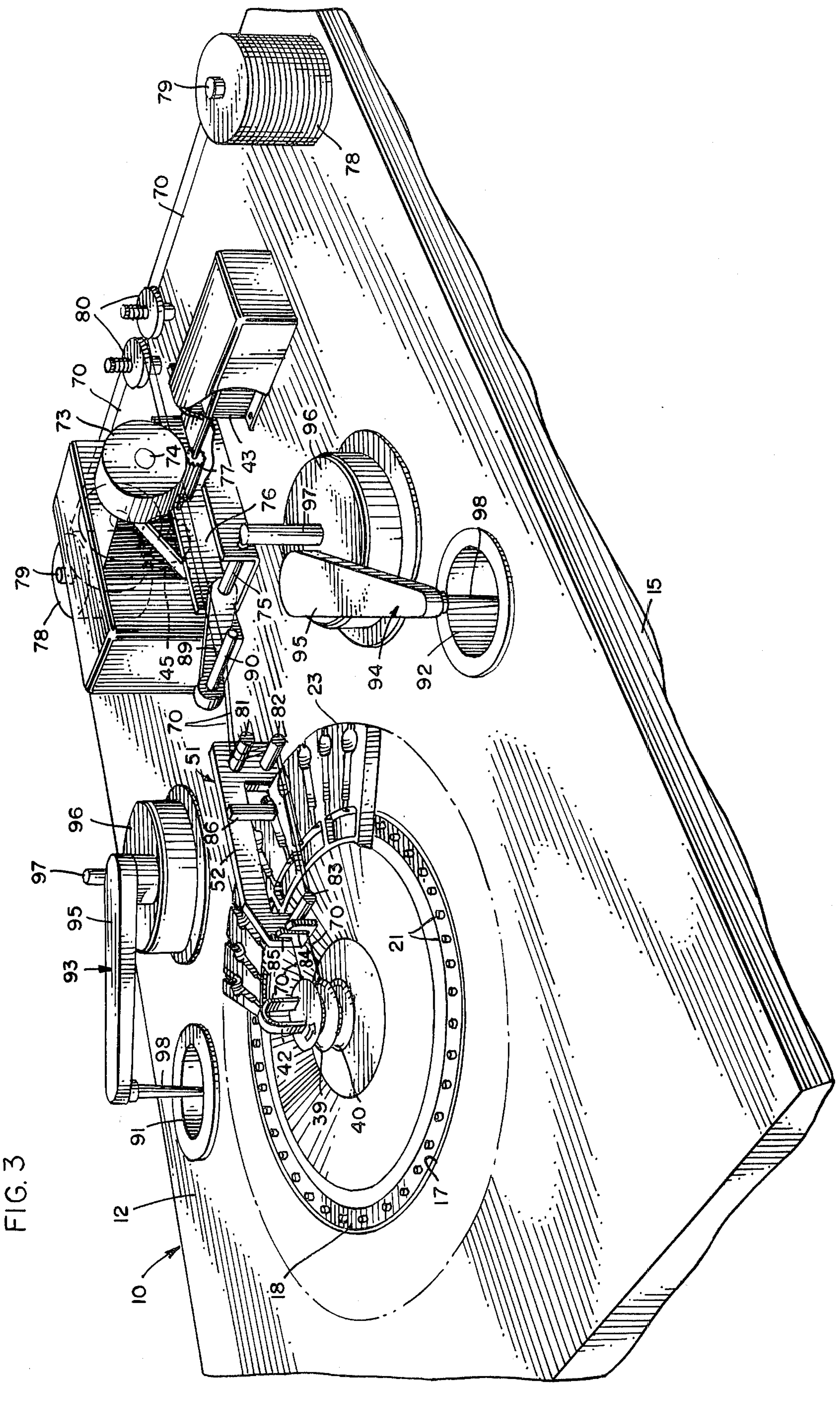
FIG. 3 is an enlarged fragmentary perspective view showing portions of the thread advancing, supporting and guiding mechanisms, the detector assembly, and the sample supporting surface, and other components disposed immediately beneath the top panel of the casing.

As the roller support arm pivots about shaft 75, the resilient roller 73 is shifted between a lowered position (FIG. 13), in which its periphery is in direct contact with the knurled shaft or capstan 77, and a raised position wherein the roller and shaft are spaced apart (FIGS. 14 and 15). Shaft 77 is power driven at constant speed and, in the embodiment illustrated, constitutes a portion of the shaft of motor 43 (FIG. 3). Pulley 45 is mounted upon an extension of that same shaft and, as previously described, the pulley 45 and belt 44 operate at constant speed regardless of rotational resistance imposed on take-up reels 39 and 40.

Referring to FIG. 3, filaments 70 are supplied by a pair of spools 78 supported upon upstanding spindles 79. The filaments pass between the plates of spring tensioners 80 and then towards take-up reels 39 and 40. Guide arm 52, and resilient roller 73 and shaft 77, are interposed between the take-up reels 39–40 and the tensioning elements 80. The driving force for advancing the filaments is transmitted by the take-up reels and the rate at which such reels advance the filaments, in the absence of a restraining force capable of causing clutches 49 and 50 to slip, is greater than the peripheral speed of the shaft or capstan 77. Consequently, when resilient roller 73 is lowered to force filaments 70 into firm engagement with shaft 77, the rate of advancement of the filaments is controlled or metered by constant-speed shaft 77. When roller 73 is raised, the filaments are again free to advance at the full rate capable of being produced by power-driven take-up reels 39 and 40. It is to be noted that when resilient roller is raised, thereby rendering the shaft 77 inoperative to control or meter the rate of travel of the filaments, the speed of advancement of such filaments will vary slightly depending on the extent of material already wound upon the take-up reels, but that when the resilient roller is lowered and the rate of filament advancement is controlled by constant-speed shaft 77, the travel of the filaments is not only substantially slower but is maintained precisely at a uniform predetermined level.

Arm 52 bridges the tray-supporting portion of the turntable and is provided with lateral guide bars or members 81-83 for guiding the paired filaments over the recess of a tray and for urging the filaments into the paired grooves or notches 30 at opposite ends of that recess. At the forward end of the guide arm 52 are a pair of upwardly projecting fingers defining slots 84 and 85 for guiding each thread towards its respective take-up reel. Intermediate the front and rear ends of the generally horizontal arm 52 is a light source 86 positioned to align precisely with one of the vertical openings 33 in the recessed bottom surface of a tray (FIG. 10) when the arm is in the lowered position shown in FIG. 13. A photocell 87 (FIGS. 13 and 17) disposed in vertical alignment with light source 86, is mounted on frame 57, the top panel 12 of the casing being provided with an aperture 88 in register with the light source and photocell to permit a beam of light to pass directly between the source and the photocell.

To avoid slack in the filaments regardless of arm movement or position, a tensioning force is applied to the filaments at all times. The tensioning member consists of a bar 89 pivotally connected at one end to shaft 75 for swinging movement in a vertical plane and provided at its opposite end with a lateral finger element 90 which rests upon both filaments (FIG. 3). The weight of the bar and its lateral member exerts a downward force on the filaments 70 to maintain the filament stretches between take-up reels 39–40 and spring resistance devices 80 under a desired degree of tension.

Figure 2:
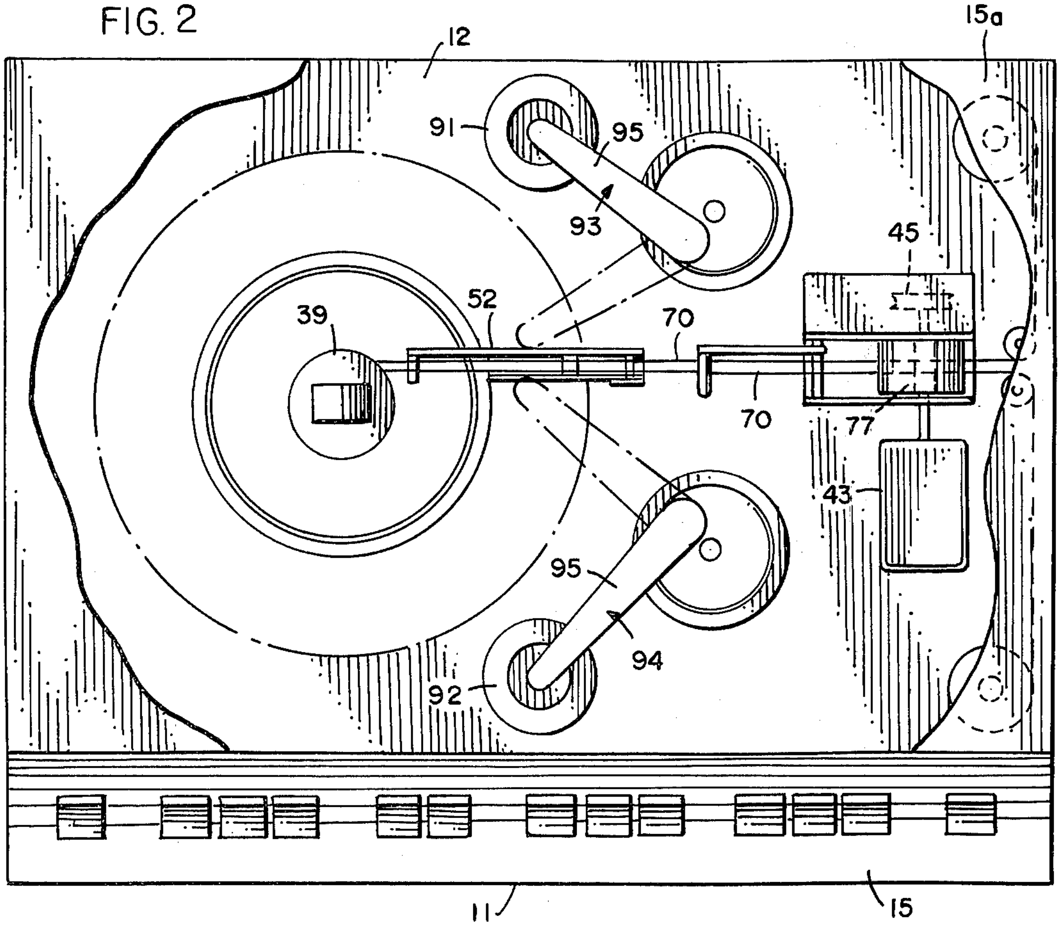
FIG. 2 is a somewhat diagrammatic top plan view of the apparatus illustrating the relationship of parts.

The addition of fluids to the wells 28 of the trays may be automatic, semi-automatic, or manual, although it has been found that a semi-automated operation, wherein the test samples are manually placed in a tray and the subsequent addition of one or more reagents is performed automatically by the apparatus, is particularly effective. Referring to FIG. 3, a pair of reagent cups 91 and 92 are disposed adjacent opposite sides of the turntable and delivery means 93 and 94 are provided for transferring measured amounts of reagent from one or both cups to the well of a tray disposed beneath arm 52. Each transferring means includes a pipetting arm 95, mounted on a power-operated turret 96 for vertical movement along a spindle 97 and for horizontal rotation between the mixing withdrawing position illustrated in FIGS. 1–3 and the dispensing position illustrated in broken lines in FIG. 2. Since the turret construction constitutes no part of the present invention, and since any of a number of well known mechanisms might be used for automatically transferring reagents from the cups to the wells of the trays, and further, since such operations might be performed manually, discussion of the details of the transfer mechanism and its operation is believed unnecessary herein.

It should be noted, however, that FIG. 3 illustrates each pipetting arm 95 in a normal rest position with its pipetting tip 98 extending downwardly into an open-topped cup 91 (or 92). In that position, the pipetting tip is not only ready to draw a measured amount of reagent, but also serves as a stirrer for gently mixing the contents of each cup. Such mixing occurs not because of movement of the pipette tip, but because of oscillation of the cup while the stationary pipette tip projects downwardly into the contents of that cup.

Figure 17:
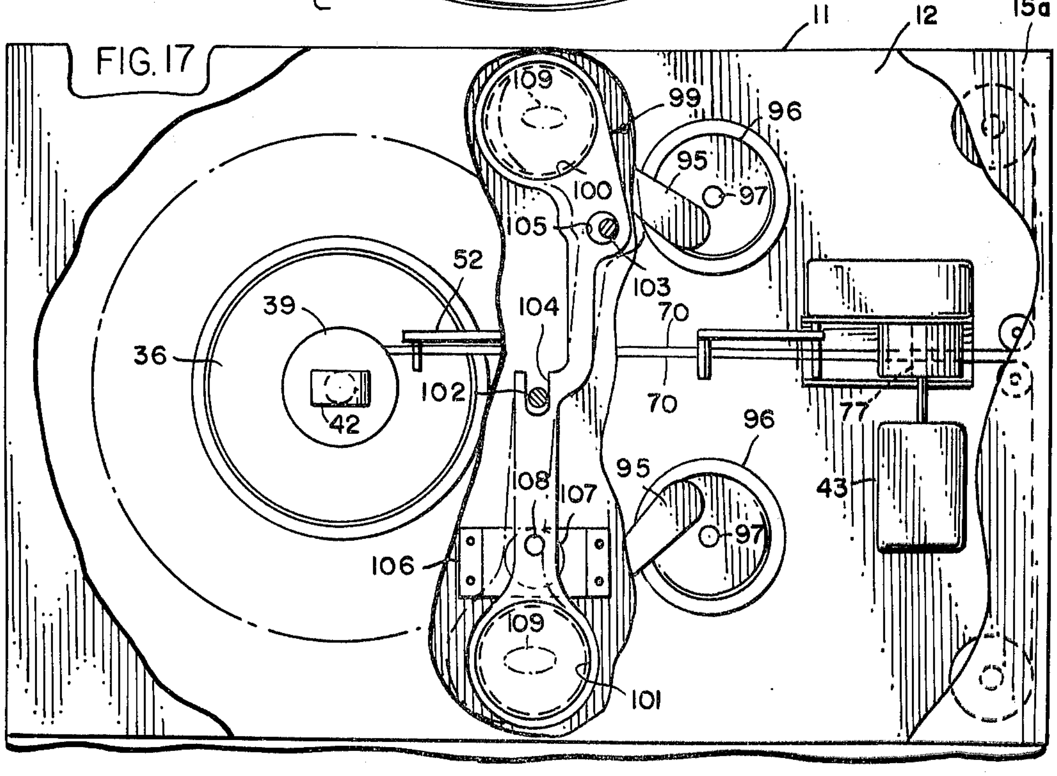
FIG. 17 is a fragmentary plan view illustrating the reagent receptacles and the means for gently agitating their contents.

The oscillating mechanism is shown in FIG. 17. A cup support bar or member 99 extends horizontally beneath top panel 12 and is provided at opposite ends with openings 100 and 101 for removably receiving cups 91 and 92. Horizontal movement of the member is limited by pins 102 and 103, both of which are rigidly secured to panel 12. Pin 102 is centrally disposed between the cups and is received within a slot 104 whereas pin 103 is disposed intermediate the central point and one of the cups (91) and is loosely received within enlarged opening 105. Adjacent the opposite end of the member is a motor 106 with a disk 107 rotated by its drive shaft. The disk is provided with an eccentric pin 108 journaled in a portion of member 99 adjacent cup-receiving recess 101. As the motor operates, eccentric shaft 108 causes each cup recess 100 and 101, and the cups disposed therein, to execute an elliptical orbit represented in FIG. 7 by broken lines 109. Consequently, a relatively gentle and highly effective stirring action is achieved during operation of the apparatus by the oscillatory movement of the cups and their contents with respect to the temporarily stationary pipette tips 98 projecting downwardly into the cups.

In operation of the apparatus, a technician first places a small quantity of blood, plasma, or other fluid capable of coagulating, into one or more wells 28 of an arcuate tray 23. The tray is then placed upon turntable 18 so that as the turntable indexes forwardly a recess containing a test sample will move into position beneath arm 52. The arm lowers into the position illustrated in FIG. 3, with the paired filaments fitting into grooves 30 to the full depth of those grooves.

Figure 4:
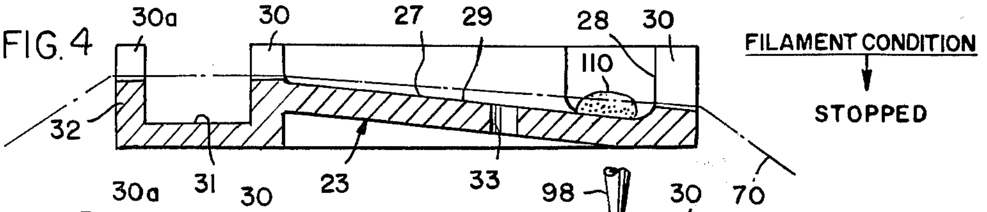
FIGS. 4–9 are schematic views illustrating the sequence of steps in the operation of the apparatus.

The sequence of operation is schematically illustrated in FIGS. 4-9. The body of clottable fluid is designated by the numeral 110 and, as shown in FIG. 4, that fluid body, which is ordinarily of the order of one or two drops in volume, rests on the slightly-inclined, and hydrophobic surface of well 28. The paired filaments extend through the well and through the body of fluid, but such filaments remain stationary until the coagulation process is initiated.

Figure 5:
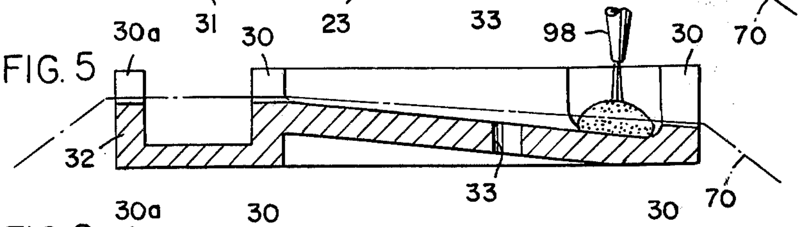

Initiation of the process leading to coagulation occurs upon the addition of a suitable coagulating agent. Where more than one agent is to be added, the one that is added last should be the coagulating agent. Thus, in a partial thromboplastin time test, two reagents are used, first a cephaloplastin reagent and then a calcium chloride reagent, the latter bein regarded as the coagulation initiator. Such reagents are stored within the receptacles or cups 91 and 92, are agitated by oscillation of those cups relative to pipette tips 98, and are transferred to the well 28 by transfer mechanisms 93 and 94. FIG. 5 illustrates pipette tip 98 at the instant it discharges a measured quantity (typically 0.1 milliliter) into a well 28 and directly into the body of clottable fluid 110 contained therein. The discharge should be forceful enough to promote mixing of the reactants.

The instant such discharge and mixing takes place, motor 43 is energized and take-up reels 39 and 40 commence drawing the fibrous filaments through the fluid mixture. Precise control of the rate of movement of such filaments is achieved by knurled shaft 77, which serves as a throttling capstan, and resilient roller 73 which maintains the filaments in contact with the knurled shaft.

Figure 6:
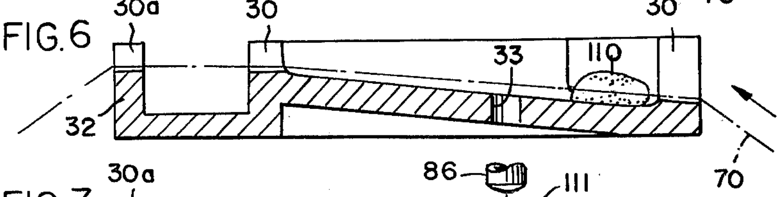
Figure 7:
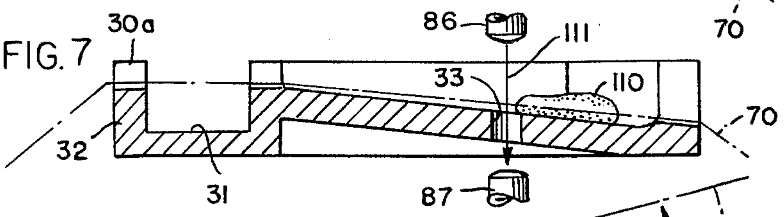

Movement of the filaments continues at a constant rate, as schematically depicted in FIG. 6, until a clot develops, clings to the filaments, and advances up the inclined pathway beyond the edge of opening 33 (FIG. 7). The instant that light beam 111 is interrupted by the clot, thread movement is stopped and the interval from the beginning to the end of such movement is measured as a direct indication of the clotting time for the sample. Preferably the interval is measured, displayed, and recorded by any suitable timing and recording devices as well known in the art, such a device being diagrammatically represented in FIG. 1 and designated by numeral 120.

Figure 11:
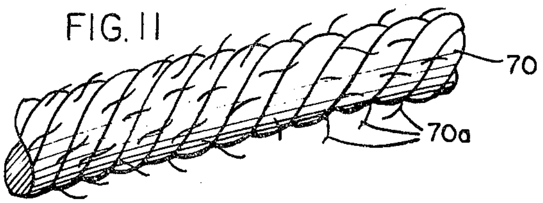
FIG. 11 is a magnified perspective view illustrating the fibrous nature of the filament.

In the operation of the apparatus, the use of filaments of fibrous character has been found particularly important. The fibrous nature of a typical filament 70 is illustrated in FIG. 11, such filament being shown in greatly magnified condition. Various grades of cotton thread have been found effective for this purpose, but filaments formed of other fibrous materials should also be suitable. By fibrous, it is meant that the filament is formed of a multiplicity of fibers which are twisted together and which have hair-like end portions **70*a*** projecting from the body of the filament. Such projections are not only believed to play an important part in the attachment of a clot to the filament, but also promote more complete mixing of the reactants during the test procedure.

Figure 12:
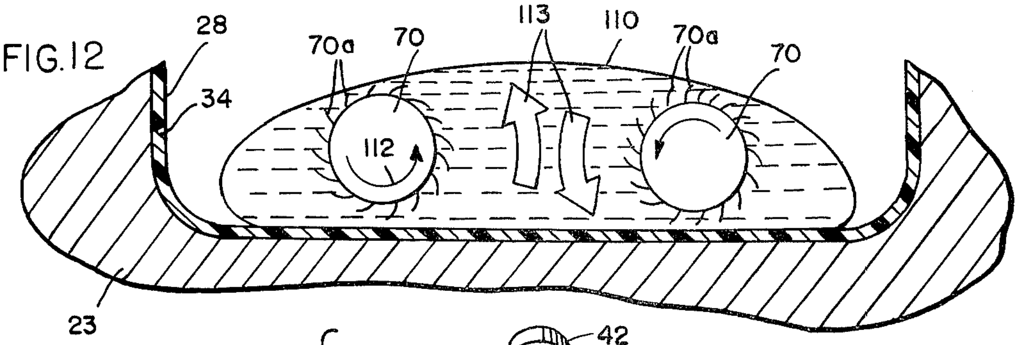
FIG. 12 is a magnified and somewhat schematic sectional view depicting the manner in which the filaments promote mixing of a sample with the reagent which activates coagulation.

FIG. 12 schematically illustrates how such mixing is promoted. It has been found that as the twisted filaments advance, a rotational movement occurs as indicated by arrows 112. Such rotation takes place because of the twisted nature of each fibrous filament and because such filament is being drawn over and about various guides as it travels from supply spool 78 to take-up reel 39 (or 40). The rotation of the filaments induces movement within fluid body 110 in the manner indicated by arrows 113. The mixing action caused by such filament rotation is enhanced where two filaments are used because, as shown in FIG. 12, the fluid is forced in opposite directions within the central zone of the body 110.

While blood, plasma, or other clottable fluids are capable of clinging to a single filament when a clot is developed, the use of paired filaments is important because more precise control over clot movement and orientation can be achieved. Specifically, as the clot develops, the bulk of its mass is disposed between the spaced filaments. The light source 86 of the detector system directs its beam between the filaments and through opening 33. Consequently, the beam is directly in the path of the major portion of a clot pulled along by the spaced filaments. In determinations where fractions of a second are meaningful, the precision and reproducibility achieved by a two-filament arrangement are of considerable significance.

Figure 8:
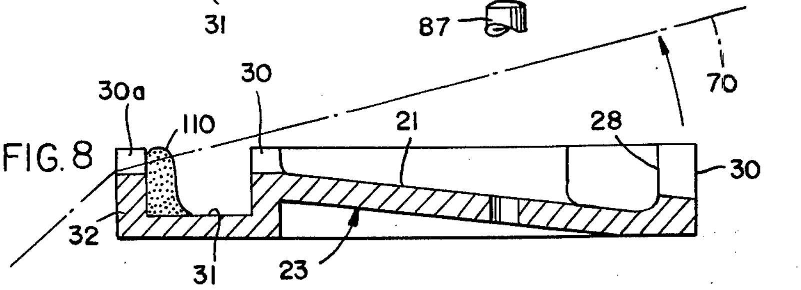
Figure 9:
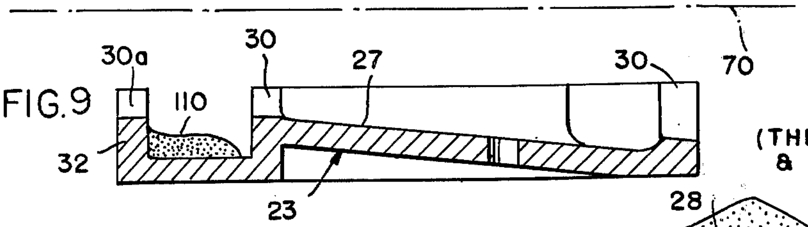

After the clot has been detected, motor 25 drives timing cam 24 through one complete revolution. As cam movement commences, the rear end of arm 52 is lifted so that filaments 70 assume the inclined condition shown in FIG. 8. During the lifting operation, resilient roller 73 is removed from capstan 77 (FIG. 14) so that the take-up reels 39 and 40 may advance the filaments at a relatively rapid rate without the resistance previously imposed by the capstan. While the inclined filaments are shown in FIG. 8 to be lifted free of grooves 30 at both ends of the recess 27, the slope of the filaments may be reduced, if desired, so that such filaments clear the grooves adjacent well 28 but still pass through the grooves 30 adjacent channel 31. In any event, the inclined filaments must pass through grooves 30*a* in inner wall 32 of the tray. The result is that the clot carried by the filaments is lifted free of the recess, any liquid supported by the filaments tends to drain downwardly along those filaments (and away from the fresh uncontaminated filament stretches therebehind), and the gelatinous mass is rapidly advanced toward channel 31 where it is stripped off of the filaments by the grooved inner barrier wall 32 (and by that wall portion providing grooves 30 adjacent the channel 31 in those constructions in which the inclined filaments may continue to pass through those grooves).

In the final stage of the operation, indexing cam 24 is rotated to a point where the front portion of the guide arm 52 is also lifted (FIG. 25). The indexing cam engages the next tooth of indexing gear 26 to rotate the turntable and the tray beneath the raised filaments. The filaments continue their rapid advance until fresh sections of the paired filaments are brought into position above the next recess in the tray, the arm 52 and filaments 70 supported thereby are then lowered into the position illustrated in FIG. 4, and the entire process is repeated.

While most of the coagulum is stripped from the filaments and deposited in the trough or channel 31 of the tray, some portion of it necessarily remains on the filaments and is carried toward the take-up reels. Should any fluid drip from the filament sections afer they are lifted free from the tray and before they are wound upon the take-up reels, such material would be expected to be collected by drip pan 36. Finally, when the filament supply is exhausted from spools 78, or at any other convenient time, the entire take-up reel and drip pan assembly is lifted (by handle 42) from the apparatus and is discarded for disposal by incineration. An operator may therefore avoid direct contact with all of the fluids involved in the test procedure and thereby avoid dangers of contamination which might otherwise arise.

While in the foregoing, an embodiment of the invention has been disclosed in considerable detail for purposes of illustration, it will be understood by those skilled in the art that many of these details may be varied without departing from the spirit and scope of the invention.

I claim:

1. A method for determining the coagulation time for a body of fluid, supported on a non-wettable surface, following the intermixing of a coagulation agent with said fluid, comprising the steps of drawing a filament through said fluid body at a predetermined rate, and detecting when said body clings to said filament and commences to move therewith along and upon said surface, the interval between intermixing of said fluid and agent and the commencement of movement of said body bearing a direct relation to the actual coagulation time of said fluid.

2. The method of claim 1 in which said filament is fibrous, at least some of the fibers thereof having end portions projecting outwardly from said filament.

3. The method of claim 1 wherein there is the further step of measuring the time interval between the intermixing of said fluid and agent and the commencement of movement of said body along said surface.

4. The method of claim 1 in which said surface is generally smooth.

5. The method of claim 1 in which said detecting step includes detecting the interruption of a beam of light by said body upon movement thereof by said filament.

6. A method for determining the coagulation time of a fluid following the addition of a coagulating agent thereto, comprising the steps of supporting a body of said fluid upon a non-wettable surface, introducing a coagulating agent into said body to initiate a coagulation reaction, simultaneously drawing a filament at a predetermined velocity through said body, and detecting when said body clings to said filament and commences to move therewith along and upon said surface.

7. The method of claim 6 wherein said filament is fibrous, at least some of the fibers thereof having end portions projecting outwardly from said filament.

8. The method of claim 6 wherein there is the further step of measuring the time interval between the intermixing of said fluid and agent and the commencement of movement of said body along said surface.

9. The method of claim 6 in which said detecting step is performed photoelectrically.

10. The method of claim 9 in which said photoelectric detection includes the interruption of a beam of light by said body as the same commences to move with said filament.

11. An apparatus for determining the coagulation time of a fluid following the intermixing of that fluid with a coagulating agent, said apparatus having a non-wettable surface having a portion for supporting a liquid body consisting essentially of a mixture of said fluid and agent, said surface also providing a pathway leading from said supporting portion, a filament, means supporting said filament for movement along a line extending over said supporting portion and along said pathway, and means coacting with said first-mentioned means for longitudinally moving said filament at a predetermined rate.

12. The apparatus of claim 11 in which means are provided for detecting when said body clings to said filament and commences to move along and upon said pathway.

13. The apparatus of claim 11 in which said filament is fibrous, at least some of the fibers thereof having end portions projecting outwardly from said filament.

14. The apparatus of claim 12 in which said detecting means includes a light source for directing a beam towards said pathway, and a photocell for detecting the interruption of said beam by said body as the same commences movement along said pathway.

* * * * *